United States Patent [19]

Gymer et al.

[11] Patent Number: 4,585,778

[45] Date of Patent: Apr. 29, 1986

[54] TRIAZOLE ANTIFUNGAL AGENTS

[75] Inventors: Geoffrey E. Gymer; Kenneth Richardson, both of Canterbury, England

[73] Assignee: Pfizer Inc., New York, N.Y.

[21] Appl. No.: 697,602

[22] Filed: Feb. 1, 1985

Related U.S. Application Data

[62] Division of Ser. No. 499,709, May 31, 1983, Pat. No. 4,507,484.

[30] Foreign Application Priority Data

Jul. 24, 1982 [GB] United Kingdom ................. 8221477

[51] Int. Cl.⁴ ..................... A01N 43/40; A01N 43/64; A61K 31/445; A61K 31/41
[52] U.S. Cl. .................................... 514/326; 514/383
[58] Field of Search ................. 424/269; 514/326, 383

[56] References Cited

FOREIGN PATENT DOCUMENTS 0061835 10/1982 European Pat. Off.

*Primary Examiner*—Jerome D. Goldberg
*Attorney, Agent, or Firm*—Charles J. Knuth; Albert E. Frost; Robert K. Blackwood

[57] ABSTRACT

Triazole antifungal agents of the formula:

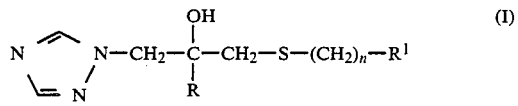

and their O-esters and O-ethers, where

R is a phenyl group optionally substituted by 1 to 3 substituents each independently selected from halo, $CF_3$, $C_1$-$C_4$ alkyl and $C_1$-$C_4$ alkoxy;

$R^1$ is selected from (a)

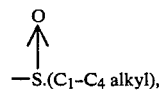

(b) —$SO_2(C_1$-$C_4$ alkyl), (C) —$SO_2NR^2R^3$ where either $R^2$ and $R^3$ are both $C_1$-$C_4$ alkyl, or $R^2$ and $R^3$ together with the N atom to which they are attached represent piperidino, (d) —$NHSO_2(C_1$-$C_4$ alkyl) and (e) —$CONR^4R^5$ where either $R^4$ is H or $C_1$-$C_4$ alkyl and $R^5$ is $C_1$-$C_4$ alkyl, or $R^4$ and $R^5$ together with the N atom to which they are attached represent piperidino;

and n is 1 or 2 with the proviso that n is 2 when $R^1$ is —$NHSO_2(C_1$-$C_4$ alkyl);

and their pharmaceutically acceptable salts. The compounds are useful as human and agricultural fungicides.

32 Claims, No Drawings

TRIAZOLE ANTIFUNGAL AGENTS

This is a division of application Ser. No. 499,709, filed on May 31, 1983, now U.S. Pat. No. 4,507,484.

BACKGROUND OF THE INVENTION

This invention relates to novel triazole derivatives which have antifungal activity and are useful in the treatment of fungal infections in animals, including humans, and as agricultural fungicides.

European patent appln. No. 82,300,888.3, published Oct. 6, 1982 as publication No. 0,061,835, broadly describes a large series of S- and O-ethers of 2-aryl-3-mercapto (or 3-hydroxy)-1-(1H-1,2,4-triazol-1-yl)propan-2-ols, and of the corresponding sulfoxides and sulfones of said mercapto derivatives, as antifungal agents.

Related S-ethers of 2-aryl-3-mercapto-1-(1H-1,2,4-triazol-1-yl)propan-2-ols as antifungal agents are described in our earlier U.S. application Ser. No. 479,524, filed Mar. 28, 1983 for "Antifungal S-Ethers of 2-Aryl-3-mercapto-1-(1H-1,2,4-triazol-1-yl)propan-2-ols"; as well as U.S. application Ser. No. 479,525, filed Mar. 28, 1983 for "Triazole Antifungal Agents" by Richardson and Whittle; and U.S. application Ser. No. 479,526, filed Mar. 28, 1983 for "Antifungal S-Arylmethyl- and S-Heterocyclylmethyl Ethers of 2-Aryl-3-mercapto-1-(1H-1,2,4-triazol-1-yl)propan-2-ols", by Richardson, Whittle and Cooper.

SUMMARY OF THE INVENTION

According to the invention, there are provided compounds of the formula:

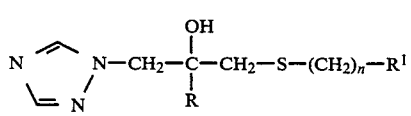  (I)

and their O-esters and O-ethers; where

R is a phenyl group optionally substituted by 1 to 3 substituents each independently selected from halo, $CF_3$, $C_1-C_4$ alkyl and $C_1-C_4$ alkoxy;

$R^1$ is selected from (a)

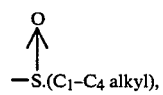

(b) $-SO_2(C_1-C_4 \text{ alkyl})$, (c) $-SO_2NR^2R^3$ wherein either $R^2$ and $R^3$ are both $C_1-C_4$ alkyl, or $R^2$ and $R^3$ together with the N atom to which they are attached represent piperidino, (d) $-NHSO_2(C_1-C_4 \text{ alkyl})$ and (e) $-CONR^4R^5$ where either $R^4$ is H or $C_1-C_4$ alkyl and $R^5$ is $C_1-C_4$ alkyl, or $R^4$ and $R^5$ together with the N atom to which they are attached represent piperidino;

and n is 1 or 2; with the proviso that n=2 when $R^1$ is $-NH-SO_2(C_1-C_4 \text{ alkyl})$;

and their pharmaceutically acceptable salts.

The O-ethers of the alcohols of the formula (I) include, for example, the $C_1-C_6$ alkyl, ($C_2-C_4$ alkenyl)methyl, ($C_2-C_4$ alkynyl)methyl, aryl (e.g. phenyl) and aralkyl (e.g. benzyl optionally ring substituted by halo, $C_1-C_4$ alkyl or $C_1-C_4$ alkoxy)ethers.

The O-esters of the alcohols of the formula (I) include, for example, the $C_2-C_4$ alkanoyl and aroyl (e.g. benzoyl, optionally substituted by halo, $C_1-C_4$ alkyl or $C_1-C_4$ alkoxy)esters.

The preferred O-ester is the acetate.

In one aspect, R is phenyl substituted by 1 or 2 substituents each independently selected from halo, $CF_3$, $C_1-C_4$ alkyl and $C_1-C_4$ alkoxy.

R is most preferably phenyl substituted by 1 to 3 substituents, especially 1 or 2 substituents, each independently selected from halo and $CF_3$.

Preferred examples of said substituted phenyl groups are phenyl substituted by 4-fluoro, 4-chloro, 4-bromo, 2,4-dichloro, 2,4-difluoro, 2,4,6-trifluoro and 4-bromo-2,5-difluoro.

"Halo" means F, Cl, Br or I.

Where appropriate, alkyl groups can be straight or branched chain.

R is most preferably 2,4-dichlorophenyl. When n is 1, $R^1$ is preferably

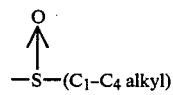

or $-SO_2(C_1-C_4 \text{ alkyl})$. When n is 2, $R^1$ is preferably $-CONR^4R^5$ where $R^4$ and $R^5$ are as defined above.

The invention also provides a pharmaceutical composition comprising a compound of the formula (I) or a pharmaceutically acceptable salt thereof, together with a pharmaceutically acceptable diluent or carrier.

The invention yet further provides an agriculturally acceptable salt of a compound of the formula (I).

The invention further provides a compound of the formula (I) or a pharmaceutically acceptable salt thereof, for use in treating fungal infections in animals, including humans.

DETAILED DESCRIPTION OF THE INVENTION

The compound of the formula (I) can be made by a number of routes, including the following:

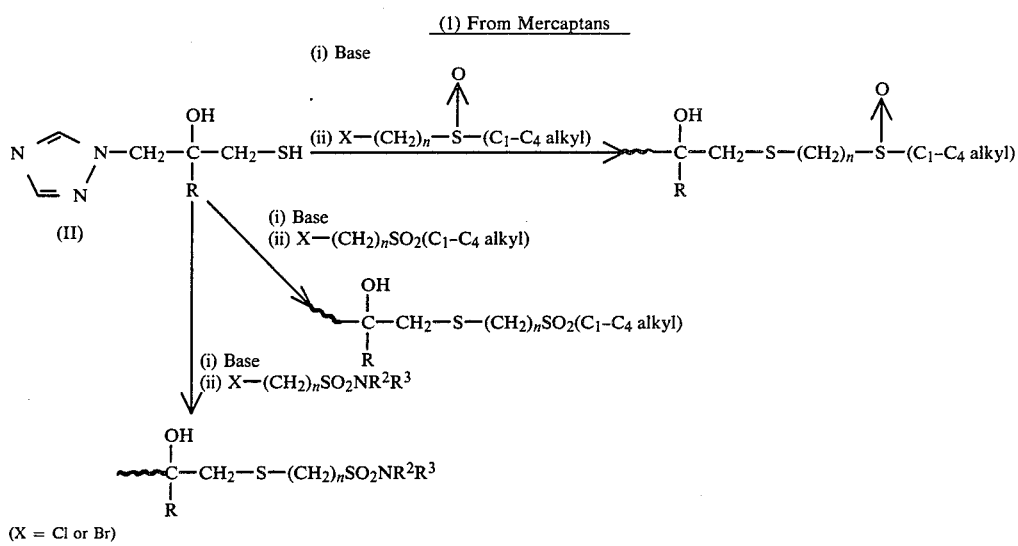

(1) From Mercaptans (X = Cl or Br)

In a typical solution, the thiol (II) in a suitable solvent, e.g. THF or DMF, is stirred with a base such as sodium hydride for a few minutes. The halo-compound is then added, and either the reactants are stirred together at room temperature for up to about 18 hours, or they are heated together for a shorter period, e.g. 3 hours under reflux, to accelerate the reaction. The product can be isolated and purified by conventional procedures.

The required compounds of the formula (II) can be prepared as follows:

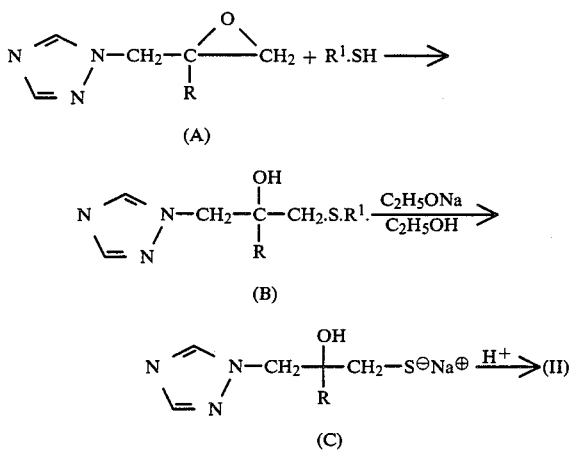

wherein R is as defined above and $R^1$ is $C_2$-$C_4$ alkanoyl, preferably acetyl.

It is preferred to carry out the reaction (A)→(B) in an organic solvent in the presence of a base, e.g. sodium hydroxide, sodium hydride or potassium carbonate. Preferred base/solvent combinations are NaH/tetrahydrofuran, NaH/DMF and NaOH/dioxan. The reaction is typically achieved by mixing the reactants together in the organic solvent with, if necessary, heating at up to 120° C., until the reaction is complete, generally in 24 hours or less. The product can be isolated and purified by conventional procedures. In this process, a mixture of the compound (B) and its O-alkanoyl derivative may be formed. These can be separated by chromatography according to known techniques.

The deacylation reaction is typically carried out by adding the alkanoyl derivative (B) dropwise to a stirred and cooled solution of sodium ethoxide in ethanol. After about an hour the resulting mixture is poured in aqueous acid, e.g. 1N hydrochloric acid, followed by neutralisation, e.g. by the addition of solid sodium bicarbonate. The thiol product (II) can again be isolated and purified by conventional procedures.

The required oxiranes (A) can be obtained by conventional methods, typically from the corresponding ketones:

$$\underset{(A)}{\underset{\underset{N}{\overset{N}{\diagdown}}}{N}-CH_2-\overset{O}{\underset{R}{C}}}$$

by reacting them in a suitable solvent (e.g. dry dimethylsulphoxide) with dimethyloxosulphonium methylide prepared from trimethylsulphoxonium iodide and either sodium hydride or cetyltrimethylammonium bromide (cetrimide) and sodium hydroxide in toluene/water.

The reaction using sodium hydride is typically achieved by adding dry powdered trimethylsulphoxonium iodide to a suspension of sodium hydride in dimethylsulfoxide. After stirring for, say, 30 minutes at room temperature, the ketone is added in an approximately equimolar amount in dimethylsulphoxide. The reaction mixture may be warmed to accelerate the reaction and after several hours at 50°-80° C., the product can be isolated by conventional procedures.

The reaction utilising cetrimide is typically achieved as follows. The ketone, trimethylsulphoxonium iodide and cetrimide are stirred vigorously in a mixture of toluene and sodium hydroxide solution for about an hour at up to about 100° C. The oxirane product can then be isolated by conventional procedures.

When R is a phenyl group containing no ortho substituent, the cetrimide route should be used.

The ketones are either known compounds or can be prepared by procedures analogous to those of the prior art. The preparation of 2-(1H-1,2,4-triazol-1-yl)-2',4'-dichloroacetophenone from 2-bromo-2',4'-dichloroacetophenone, 1,2,4-triazole and potassium carbonate is for example, described in Example 1 of British patent specification No. 1,512,918, which utilises acetonitrile as the solvent under reflux for 20 hours. We have found that this type of reaction is generally best carried out in acetone at 0°–20° C., when it is generally complete in a shorter period of time, e.g. 4 hours or less.

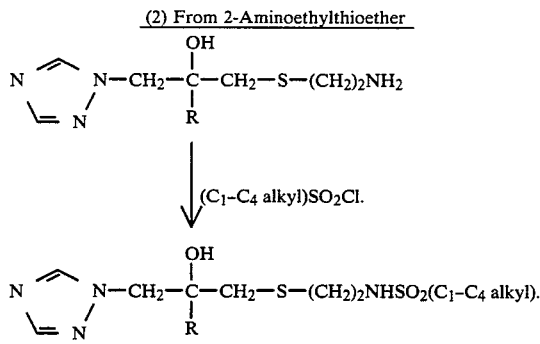

The reaction is typically carried out at low temperature (e.g. 5° C.) in an organic solvent such as pyridine. The product can then be isolated and purified conventionally. The sulphonyl chloride starting materials are available conventionally.

The preparation of a typical amine starting material is described in the experimental section.

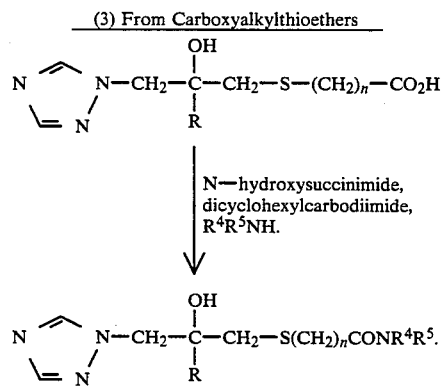

In a typical procedure the acid is suspended in a suitable solvent, e.g. dioxan, and N-hydroxysuccinimide and dicyclohexylcarbodiimide are added. After stirring for a few hours at room temperature, the amine is added, and stirring is continued for a short period, e.g. 30 minutes, following which the product can be isolated conventionally. The amine starting materials are available conventionally. The preparation of a typical acid starting material is described in the experimental section.

(4) The ethers can be made conventionally, e.g. by treating an alkali metal salt of the alcohols of the formula (I), e.g. a lithium or sodium salt, with the appropriate halide, e.g. an alkyl, alkenyl, alkynyl or aralkyl halide. Esters can be made by treating an alkali metal salt of compound (I) with the appropriate acid chloride, bromide or anhydride.

Where the compounds of the invention contain an optically active centre or centres, the invention includes both the resolved and unresolved forms.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their pharmaceutically acceptable salts are anti-fungal agents, useful in combating fungal infections in animals, including humans. For example they are useful in treating topical fungal infections in man caused by, among other organisms, species of Candida, Trichophyton, Microsporum, or Epidermophyton, or in mucosal infections caused by Candida albicans (e.g. thrush and vaginal candidiasis). They can also be used systemically in the treatment of systemic fungal infections caused by, for example, Candida albicans, Cryptococcus neoformans, Aspergillus fumigatus, Coccidioides, Paracoccidioides, Histoplasma or Blastomyces.

The in vitro evaluation of the anti-fungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration are inoculated with a standard culture of, for example, Candida albicans and each plate is then incubated for 48 hours at 37° C. The plates are then examined for the presence or absence of growth of the fungus and the appropriate m.i.c. value is noted. Other micro-organisms used in such tests can include Cryptococcus neoformans, Aspergillus fumigatus, Trichophyton spp; Microsporum spp; Epidermophyton floccosum, Coccidioides immitis, and Torulopsis glabrata.

The in vivo evaluation of the compounds can be carried out at a series of dose levels by intraperitoneal or intravenous injection or by oral administration, to mice which are inoculated with a strain of Candida albicans. Activity is based on the survival of a treated group of mice after the death of an untreated group of mice following 48 hours observation. The dose level at which the compounds provides 50% protection against the lethal effect of the infection is noted.

Oral $PD_{50}$ values for the compounds prepared by the Examples below in mice infected with Candida albicans are as follows:

| Example No. | $PD_{50}$ (mg./kg.) |
| --- | --- |
| 1 | 4.2 |
| 2 | 2.2 |
| 3 | ~17 |
| 4 | ~20 |
| 5 | 2.2 |
| 6 | 9.4 |
| 7 | ~20 |
| 8 | ~20. |

The most preferred individual compounds are those of Examples 1, 2 and 5.

For human use, the anti-fungal compounds of the formula (I) can be administered alone, but will generally be administered in admixture with a pharmaceutical carrier selected with regard to the intended route of administration and standard pharmaceutical practice.

For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, the daily dosage level of the anti-fungal compounds of the formula (I) (and salts, O-esters and O-ethers thereof) will be from 0.1 to 5 mg/kg (in divided doses) when administered by either the oral or parenteral route. Thus tablets or capsules of the compounds will typically contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the anti-fungal compounds of formula (I) can be administered in the form of a suppository or pessary, or they can be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be applied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

Thus the invention further provides a plant or seed antifungal composition comprising a compound of the formula (I) or an agriculturally acceptable salt thereof, together with an agriculturally acceptable diluent or carrier.

The invention yet further provides a method of treating a plant or seed having a fungal infection, which comprises contacting said plant or seed with an antifungally effective amount of a compound of the formula (I) or with an agriculturally acceptable salt thereof.

The following Examples illustrate the invention. All temperatures are in °C.:

EXAMPLE 1

Preparation of 2-(2,4-dichlorophenyl)-3-(mesylmethylthio)-1-(1H-1,2,4-triazol-1-yl)propan-2-ol, oxalate salt

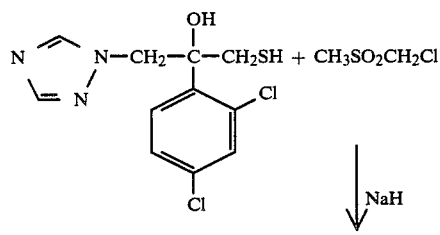

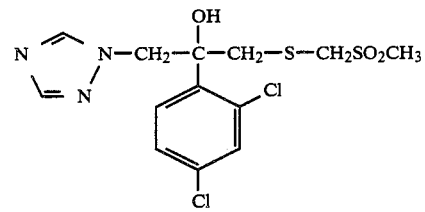

2-(2,4-Dichlorophenyl)-1-mercapto-3-(1H-1,2,4-triazol-1-yl)propan-2-ol (0.304 g) was dissolved in dry tetrahydrofuran (5 ml) and sodium hydride (58 mg of a 50% dispersion in oil, 1.2. equiv.), was added. After stirring for ten minutes, chlorodimethylsulphone (0.141 g, 1.1 equiv.) was added, and the reaction stirred overnight (18 hours). The reaction mixture was then poured into water (20 ml), and extracted with ethyl acetate (3×20 ml). The organic extracts were combined, washed with saturated sodium chloride solution, dried ($Na_2SO_4$) and evaporated to a gum, 0.55 g.

This gum was chromatographed on silica, eluting with methylene chloride, containing 5% isopropanol and 0.5% ammonium hydroxide to give a gum which formed a crystalline oxalate with oxalic acid in a mixture of ether and ethyl acetate, to give the title compound, 0.116 g, m.p. 131°-133°.

Analysis: Found: C,35.0; H,3.2; N,6.9. $C_{13}H_{15}Cl_2N_3O_3S_2.2(COOH)_2$ requires: C,35.4; H,3.3; N,7.3%.

EXAMPLE 2

Preparation of 2-(2,4-dichlorophenyl)-3-(methylsulphinylmethylthio)-1-(1H-1,2,4-triazol-1-yl)-propan-2-ol

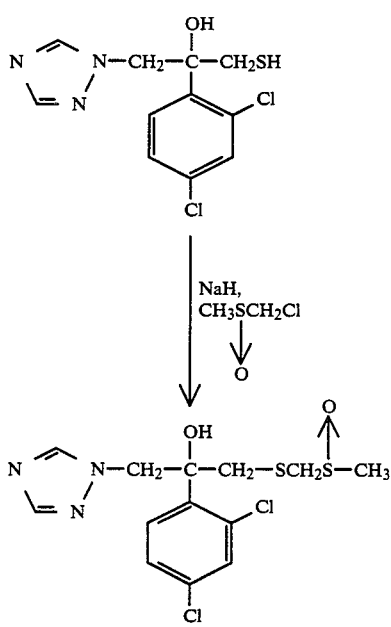

The title compound was prepared in a similar manner to Example 1 above using the above sulphinyl compound, but dry DMF was used as the solvent, and chromatography was performed using 10% isopropanol/1% ammonium hydroxide in methylene chloride. The first diastereoisomeric pair was crystallised from ethyl acetate to give the title compound, 147°–149°.

Analysis: Found: C,41.1; H,3.9; N,11.3. $C_{13}H_{15}Cl_2N_3O_2S_2$ requires: C,41.0; H,4.0; N,11.0%.

The second diastereoisomeric pair was converted to the oxalate salt, m.p. 171°–173°, and was characterised by n.m.r. and mass spectroscopy.

EXAMPLE 3

Preparation of 2-(2,4-dichlorophenyl)-3-(2-[mesylamino]ethylthio)-1-(1H-1,2,4-triazol-1-yl)-propan-2-ol, oxalate salt

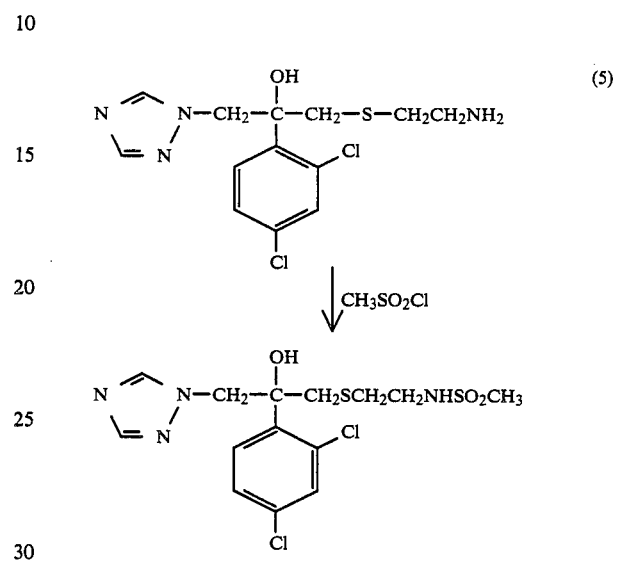

2-(2,4-Dichlorophenyl)-3-(2-aminoethylthio)-1-(1H-1,2,4-triazol-1-yl)propan-2-ol (0.347 g), was dissolved in pyridine (3 ml), the solution cooled to 5° C. in an ice bath, and methanesulphonyl chloride (0.126 g, 1.1 equiv.) was added dropwise over 5 minutes. After stirring for 30 minutes at 5° C., the mixture was poured into saturated sodium chloride solution (20 ml) and extracted with ethyl acetate (3×10 ml). The combined organic extract was washed with saturated sodium chloride solution (2×10 ml), dried ($Na_2SO_4$), and evaporated to an orange gum, 0.31 g.

This gum was chromatographed on silica, eluting with methylene chloride containing 5% isopropanol to give a colourless gum, which was converted to the oxalate salt in ethyl acetate/ether mixture. The oxalate salt was recrystallised from isopropanol/ether to give colourless crystals of the title compound, 0.173 g, m.p. 115°–118° C.

Analysis: Found: C,37.0; H,3.9; N,10.8. $C_{14}H_{18}Cl_2N_4O_3S_2.(COOH)_2$ requires: C,37.3; H,3.9; N,10.8%.

EXAMPLE 4

Preparation of
2-(2,4-dichlorophenyl)-3-(piperidinosulphonylmethylthio)-1-(1H-1,2,4-triazol-1-yl)-propan-2-ol

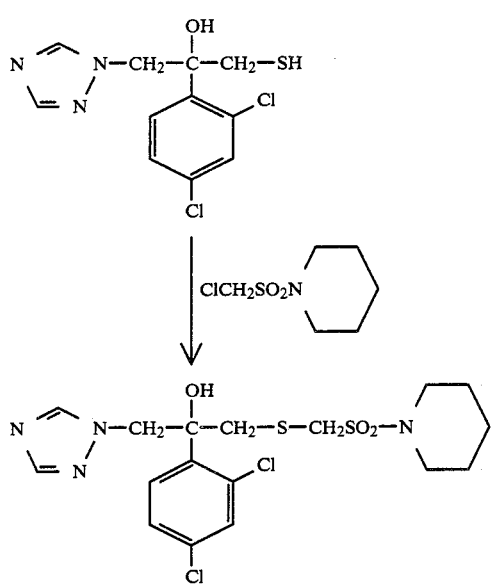

2-(2,4-Dichlorophenyl)-1-mercapto-3-(1H-1,2,4-triazol-1-yl)-propan-2-ol (0.304 g) was stirred in tetrahydrofuran (5 ml) whilst sodium hydride (58 mg of a 50% dispersion in oil, 1.2 equiv.) was added in one portion. After stirring a further five minutes, N-(chloro-methylsulphonyl)piperidine (0.296 g, 1.1 equiv.) was added and heated under reflux for 3 hours. The reaction mixture was allowed to cool to room temperature then poured into an ice/water mixture (20 ml), and extracted with ethyl acetate (3×15 ml). The organic extracts were combined, dried (Na$_2$SO$_4$) and evaporated to a gum, 0.71 g.

Chromatography on silica, eluting with ethyl acetate containing 10% methanol, gave only a partial purification. The fractions containing the product (as judged by t.l.c.) were combined and chromatographed again on silica, eluting with methylene chloride containing 5% isopropanol and 0.5% ammonium hydroxide, to give a white solid, which was recrystallised from isopropanol/ether to give colourless crystals of the title compound, 0.067 g, m.p. 126°–128°.

Analysis: Found: C,44.2; H,4.7; N,12.3. C$_{17}$H$_{22}$Cl$_2$N$_4$O$_3$S$_2$ requires: C,43.9; H,4.8; N,12.0%.

EXAMPLE 5

Preparation of
2-(2,4-dichlorophenyl)-3-(2-[N,N-dimethylcarbamoyl]ethylthio)-1-(1H-1,2,4-triazol-1-yl)-propan-2-ol hydrochloride hemihydrate

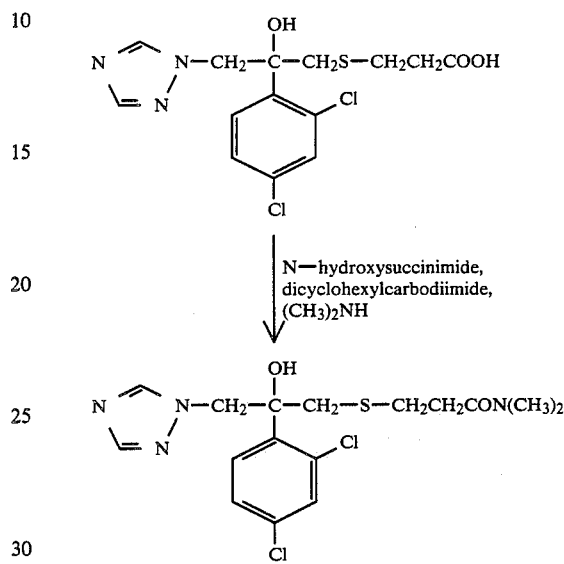

2-(2,4-Dichlorophenyl)-3-(2-carboxyethylthio)-1-(1H-1,2,4-triazol-1-yl)-propan-2-ol (0.38 g) was suspended in dioxan whilst N-hydroxysuccinimide (0.172 g, 1.5 equiv.) and dicyclohexylcarbodiimide (0.309 g, 1.5 equiv.) were added. The reaction mixture was stirred overnight (19 hours) at room temperature. Anhydrous dimethylamine (0.09 g, 2.0 equiv.) was added, and stirring continued for 30 minutes.

The precipitated dicyclohexylurea was filtered off, and the filtrate evaporated to a gum, which was dissolved in ethyl acetate (15 ml). The ethyl acetate solution was washed with saturated sodium chloride solution (3×10 ml), dried (MgSO$_4$), and evaporated to a gum, 0.53 g.

This gum was chromatographed on silica, eluting with acetone containing 20% ether. The resulting gum was converted to a hydrochloride salt in ethyl acetate, to give the title compound as a glass, 143 mg, m.p. 48°–53°.

Analysis: Found: C,42.5; H,4.3; N,12.2. C$_{16}$H$_{20}$Cl$_2$N$_4$O$_2$S.HCl.½H$_2$O requires: C,42.8; H,4.9; N,12.5%.

EXAMPLES 6–8

The following compounds were prepared similarly to the previous Example, starting from the same acid, N-hydroxysuccinimide, dicyclohexylcarbodiimide, and the appropriate amine, and were characterised as the hydrochloride salts:

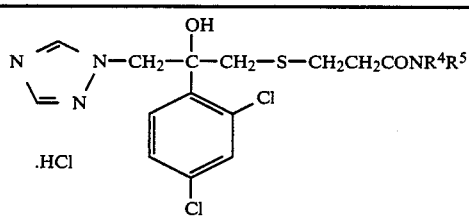

| Example No. | —NR⁴R⁵ | m.p. (°C.) | Analysis % (Theoretical in brackets) | | |
|---|---|---|---|---|---|
| | | | C | H | N |
| 6 (as ½ hydrate) | —NH(CH₂)₃CH₃ | 54–60 | 45.3 (45.3 | 5.5 5.5 | 12.4 11.7) |
| 7 (as mono- hydrate) | —N(C₂H₅)₂ | 38–41 | 44.4 (44.4 | 5.6 5.6 | 11.8 11.5) |
| 8 (as ½ hydrate) | —N⟨ ⟩ (piperidine) | 48–52 | 46.5 (46.7 | 5.1 5.4 | 11.9 11.5) |

In Example 7, the chromatography was carried out by elution with methylene chloride containing isopropanol (5%) and acetic acid (0.5%) to give a gum which was converted to the hydrochloride salt.

EXAMPLE 9

The method of Example 1, substituting the appropriately substituted mercaptan for 2-(2,4-dichlorophenyl)-1-mercapto-3-(1H-1,2,4-triazol-1-yl)propan-2-ol, yields the following compounds:

2-(2-chlorophenyl)-3-(mesylmethylthio)-1-(1H-1,2,4-triazol-1-yl)propan-2-ol;
2-(2,4-difluorophenyl)-3-(mesylmethylthio)-1-(1H-1,2,4-triazol-1-yl)propan-2-ol;
2-(3-trifluoromethylphenyl)-3-(mesylmethylthio)-1-(1H-1,2,4-triazol-1-yl)propan-2-ol;
2-(4-trifluoromethylphenyl)-3-(mesylmethylthio)-1-(1H-1,2,4-triazol-1-yl)propan-2-ol;
2-(4-chlorophenyl)-3-(mesylmethylthio)-1-(1H-1,2,4-triazol-1-yl)propan-2-ol;
2-(4-bromophenyl)-3-(mesylmethylthio)-1-(1H-1,2,4-triazol-1-yl)propan-2-ol;
2-(4-fluorophenyl)-3-(mesylmethylthio)-1-(1H-1,2,4-triazol-1-yl)propan-2-ol;
2-(2,4,6-trifluorophenyl)-3-(mesylmethylthio)-1-(1H-1,2,4-triazol-1-yl)propan-2-ol; and
2-(4-bromo-2,5-difluorophenyl)-3-(mesylmethylthio)-1-(1H-1,2,4-triazol-1-yl)propan-2-ol.

The method of Example 1, 2 and 4, substituting (propylsulfonyl)ethyl chloride, diethylaminosulfonylmethyl chloride, 2-(methylaminosulfonyl)ethyl chloride or 2-(methylsulfonyl)ethyl chloride as appropriate, yields the following compounds:

2-(2,4-dichlorophenyl)-3-(2-[propanesulfonyl]ethylthio)-1-(1H-1,2,4-triazol-1-yl)propan-2-ol;
2-(2,4-dichlorophenyl)-3-(diethylaminosulfonylmethylthio)-1-(1H-1,2,4-triazol-1-yl)propan-2-ol;
2-(2,4-dichlorophenyl)-3-(2-[methylaminosulfonyl]ethylthio)-1-(1H-1,2,4-triazol-1-yl)propan-2-ol; and
2-(2,4-dichlorophenyl)-3-(2-[mesyl]ethylthio)-1-(1H-1,2,4-triazol-1-yl)propan-2-ol.

EXAMPLE 10

The method of Examples 5–8, substituting therein the appropriate carboxylic acid and amine, yields the following compounds:

2-(2,4-difluorophenyl)-3-(2-[N,N-dimethylcarbamoyl]ethylthio)-1-(1H-1,2,4-triazol-1-yl)propan-2-ol;
2-(3-trifluoromethylphenyl)-3-(2-[N-isopropylcarbamoyl]ethylthio)-1-(1H-1,2,4-triazol-1-yl)propan-2-ol;
2-(4-chlorophenyl)-3-(2-[N,N-diethylcarbamoyl]ethylthio)-1-(1H-1,2,4-triazol-1-yl)propan-2-ol;
2-(4-bromophenyl)-3-(piperidinocarbonylethylthio)-1-(1H-1,2,4-triazol-1-yl)propan-2-ol;
2-(4-fluorophenyl)-3-(2-[N-butylcarbamoyl]ethylthio)-1-(1H-1,2,4-triazol-1-yl)propan-2-ol;
2-(4-bromo-2,5-difluoro)-3-(2-[N,N-dimethylcarbamoyl]ethylthio)-1-(1H-1,2,4-triazol-1-yl)propan-2-ol; and
2-(2,4-dichlorophenyl)-3-(piperidinocarbonylmethylthio)-1-(1H-1,2,4-triazol-1-yl)propan-2-ol.

PREPARATION 1

Preparation of 2-(2,4-dichlorophenyl)-3-(2-aminoethylthio)-1-(1H-1,2,4-triazol-1-yl)-propan-2-ol, oxalate salt

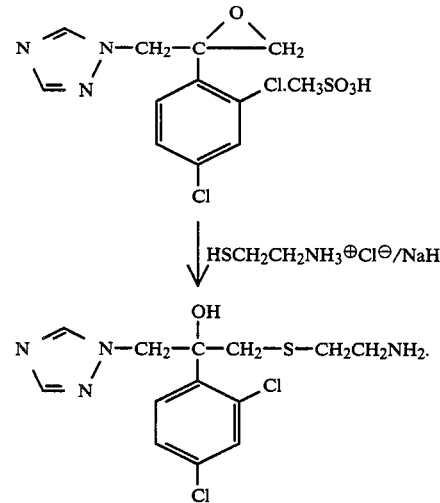

2-Aminoethanethiol hydrochloride (1.2 g) was dissolved in dimethylformamide (50 ml), cooled to 5° C., and sodium hydride (1.6 g of a 50% dispersion in oil, 3.3 equiv.) was added in portions over 10 minutes. After stirring for 15 minutes, 2-(2,4-dichlorophenyl)-2-(1H-1,2,4-triazol-1-ylmethyl)oxirane mesylate (3.60 g) was added in portions over 10 minutes. Stirring was continued overnight (20 hours) at room temperature. The reaction mixture was then poured onto ice (150 ml) and extracted with ethyl acetate (3×50 ml). The extracts were combined, dried (Na₂SO₄) and evaporated under reduced pressure to give a gum, 3.0 g.

Chromatography on silica, eluting with 10% methanol in chloroform, gave a gum 1.8 g, 52%.

A portion of this gum was converted to an oxalate salt with oxalic acid in ether to give a crystalline solid, which was recrystallised from isopropanol to give colourless crystals of the title product, m.p. 168°–170°.

Analysis: Found: C,41.3; H,4.4; N,13.3. C₁₃H₁₆Cl₂N₄OS.(COOH)₂ requires: C,41.2; H,4.1; N,12.8%.

By the same method, the appropriate oxiranes are converted to:

2-(2,4-difluorophenyl)-3-(2-aminoethylthio)-1-(1H-1,2,4-triazol-1-yl)propan-2-ol;

2-(3-trifluoromethylphenyl)-3-(2-aminoethylthio)-1-(1H-1,2,4-triazol-1-yl)propan-2-ol;

2-(4-chlorophenyl)-3-(2-aminoethylthio)-1-(1H-1,2,4-triazol-1-yl)propan-2-ol;

2-(4-bromophenyl)-3-(2-aminoethylthio)-1-(1H-1,2,4-triazol-1-yl)propan-2-ol;

2-(4-fluorophenyl)-3-(2-aminoethylthio)-1-(1H-1,2,4-triazol-1-yl)propan-2-ol; and 2-(4-bromo-2,5-difluoro)-3-(2-aminoethylthio)-1-(1H-1,2,4-triazol-1-yl)propan-2-ol.

PREPARATION 2

Preparation of 2-(2,4-dichlorophenyl)-3-(2-carboxyethylthio)-1-(1H-1,2,4-triazol-1-yl)-propan-2-ol

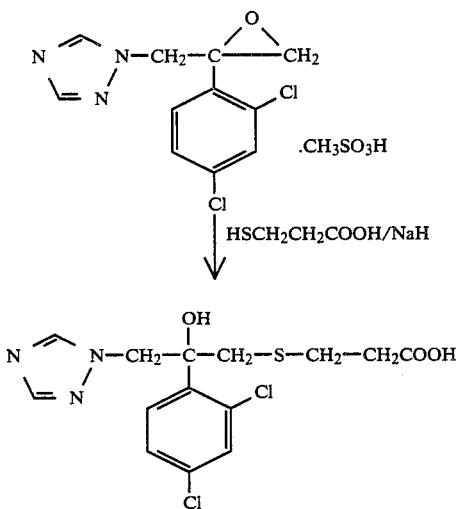

3-Mercaptopropionic acid (1.2 g, 1.1 equiv.) was dissolved in dimethylformamide (50 ml) and cooled to 5° C. in an ice bath. Sodium hydride (1.6 g of a 50% dispersion in oil, 3.3 equiv.) was added in portions over 10 minutes, followed by 2-(2,4-dichlorophenyl)-2-(1H-1,2,4-triazol-1-ylmethyl)oxirane mesylate (3.6 g). After stirring overnight (19 hours) the mixture was poured onto ice (200 ml) and extracted with methylene chloride (3×50 ml). The aqueous layer was adjusted to pH3 with hydrochloric acid (5N) and extracted with methylene chloride (3×50 ml). The organic extracts were combined, washed with saturated sodium chloride solution (2×50 ml), dried (Na₂SO₄), and evaporated under reduced pressure to a gum, 5.6 g.

This was chromatographed on silica. Elution with methylene chloride containing 10% isopropanol and 1% acetic acid gave after concentration a solid, which was recrystallised from isopropanol/ether mixture to give colourless crystals of the title compound 1.18 g, m.p. 179°–181°, 31%.

Analysis: Found: C,44.7; H,4.2; N,11.5. C₁₄H₁₅Cl₂N₃O₃S requires: C,44.7; H,4.0; N,11.2%.

PREPARATION 3

(i) Preparation of 2-(1H-1,2,4-triazol-1-yl)-2',4'-dichloro acetophenone (A)

This compound was prepared similarly to the method described in British patent specification No. 1512918:

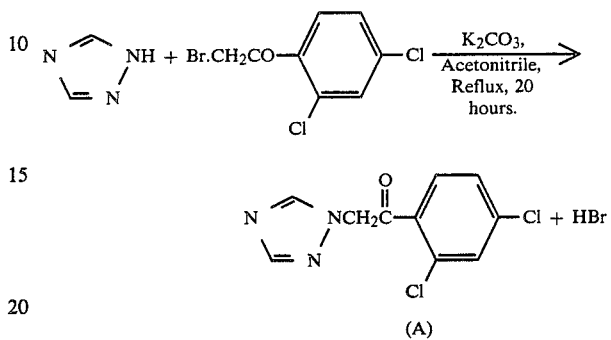

(ii) Preparation of 1-(2,4-Dichlorophenyl)-1-(1H-1,2,4-triazol-1-ylmethyl)-oxirane (B)

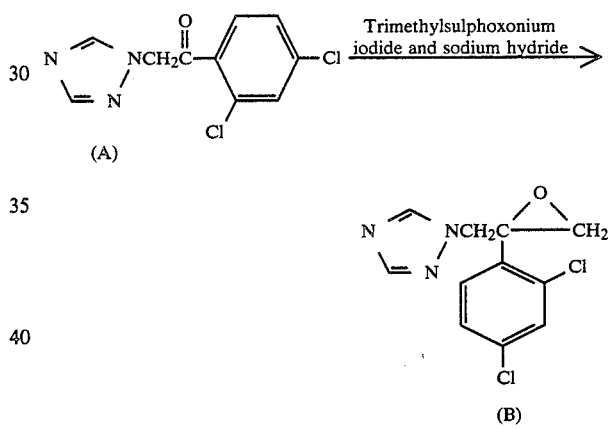

3.78 g (0.079 Mole) of sodium hydride (50% dispersion in oil) was suspended, with stirring, in 20 ml of dry ether. The ether was then removed by decantation, and the sodium hydride was dried in a stream of dry nitrogen. 100 ml of dry dimethyl sulphoxide was added followed by 17.34 g (0.079 mole) of dry powdered trimethylsulphoxonium iodide, in portions, over 15 minutes. The resulting mixture was stirred for 30 minutes at room temperature (20° C.). 18.33 g (0.072 mole) of compound (A) as a solution in 50 ml of dry dimethyl sulphoxide was then added. The mixture was heated at 60° C. for 3 hours and then stood at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether followed by evaporation of appropriate fractions gave 6.62 g (34.4%) of the title compound (B) as a gum which could not be crystallised. N.m.r. (CDCl₃) was consistent with the desired structure. Compound (B) was then converted to the mesylate conventionally using methanesulphonic acid and used directly.

PREPARATION 4

Preparation of
2-(2,4-dichlorophenyl)-2-mercapto-1-(1H-1,2,4-triazol-1-yl)propan-2-ol 2-(1H-1,2,4-triazol-1-ylmethyl)-2-(2,4-dichlorophenyl)oxirane 5 g (0.185M) was heated under mild reflux in thiolacetic acid (CH₃COSH) (5 ml) for three hours. The mixture was then cooled and added to a mixture of ice-cooled saturated sodium bicarbonate solution (200 ml) and ethyl acetate (200 ml) and the aqueous layer was separated. The organic layer was washed a further four times with ice cooled saturated sodium bicarbonate solution (200 ml in total), dried (MgSO₄) and evaporated to give a red gum which was dissolved in ethanol (20 ml). This solution was added dropwise over 15 minutes to a stirred and ice-cooled solution of sodium ethoxide (3.78 g, 0.0556M) in ethanol (100 ml). After one hour the mixture was poured into 1N hydrochloric acid (100 ml) and this solution was then neutralised by addition of solid sodium bicarbonate. Extraction with methylene chloride (6×50 ml), drying (MgSO₄), and evaporation of the combined extracts gave a gum which was chromatographed on silica, eluting with ethyl acetate, to give after one recrystallisation from ethyl acetate/hexane the title compound, yield 2.3 g, m.p., 139°–142.5° C.

Analysis %: Found: C,43.3; H,3.7; N,14.0. Calculated for $C_{11}H_{11}Cl_2N_3OS$: C,43.4; H,3.6; N,13.8.

PREPARATION 5

The following compound, m.p. 102°, was prepared according to the preceding Preparation, starting from the appropriate oxirane and thiolacetic acid, followed by deacylation using $C_2H_5ONa/C_2H_5OH/HCl$:

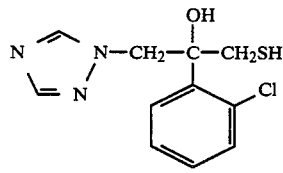

Analysis %: Found: C, 49.12; H, 4.49; N, 15.90 Calculated for $C_{11}H_{12}ClN_3OS$: C, 49.07; H, 4.46; N, 15.61.

The same method is used to prepare the 2,4-difluoro, 3-trifluoromethyl, 4-trifluoromethyl, 4-chloro, 4-bromo, 4-fluoro, 2,4,6-trifluoro and 4-bromo-2,5-difluoro substituted phenyl analogs thereof.

PREPARATION 6

(i) Preparation of 2-chloro-2',4'-difluoroacetophenone

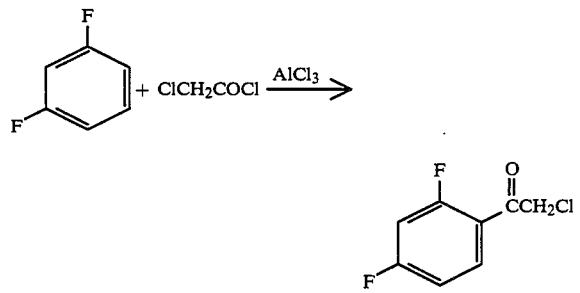

Chloroacetyl chloride (113 g, 1.0M) was added dropwise to a stirred mixture of 1,3-difluorobenzene (114 g, 1.0M) and anhydrous aluminium chloride (146.6 g, 1.1M) at room temperature (20° C.). The mixture was stirred for a further five hours at 50°–55° C. Methylene chloride (48.5 ml) was added slowly as the mixture was allowed to cool to room temperature. The methylene chloride layer was separated, washed with water (2×320 ml) and the solvent removed by distillation at reduced pressure leaving a pale yellow solid (180 g).

A portion of the crude product (145 g) was crystallised from n-hexane (435 ml) giving the title compound (113 g, 73%) m.pt. 47°–49° C. (literature* 46.5° C.). IR (KBr) and nmr (CDCl₃) were consistent with the desired structure.

*Von D. Ehlers, H. Bercher and A. Grisk, J. Prakt, Chem., 315, 1169 (1973).

(ii) Preparation of
2',4'-Difluoro-2-(1H-1,2,4-triazol-1-yl)acetophenone hydrochloride

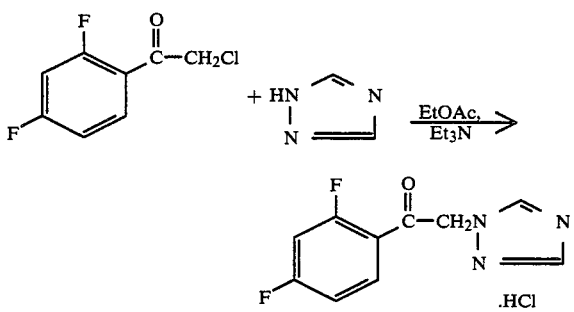

To a mixture of 1,2,4-triazole (30.4 g, 0.44M) and triethylamine (15.1 g, 0.15M) in refluxing ethyl acetate (186 ml) was added a solution of 2-chloro-2',4'-difluoroacetophenone (38.1 g, 0.2M) in ethyl acetate (80 ml). The mixture was refluxed for six hours then cooled to room temperature and the insolubles were removed by filtration. The filtrate was washed with water (2×200 ml) and then the solvent was removed by distillation at reduced pressure. The crude product was dissolved in ethyl acetate (150 ml) then 25% w/v HCl gas in isopropanol was added. The mixture was granulated at 0° C. for one hour and then the solid was collected by filtration and dried to give the title compound (21.6 g, 40%), melting point 167°–170° C. IR (KBr) and nmr (DMSO) were consistent with the desired structure.

This intermediate was characterised as the free base, which was prepared by the following technique:

To a stirred slurry of sodium bicarbonate (16.8 g, 0.2M) and 1,2,4-triazole (27.6 g, 0.4M) in refluxing toluene (180 ml) was added a solution of 2-chloro-2',4'-difluoroacetophenone (38.1 g, 0.2M) in toluene (45 ml). The mixture was stirred at reflux for three hours and the water formed during the reaction was removed using a Dean and Stark trap. The reaction mixture was cooled to room temperature and then water (180 ml) was added. The toluene layer was separated and the solvent removed by distillation at reduced pressure. The resulting pale brown solid was crystallised from 1:1 ethyl acetate:n-hexane (70 ml) giving the title compound (3.9 g), melting point 103°–105° C. The IR (KBr) and nmr (CDCl₃) were consistent with the desired structure.

Analysis %: Found: C,53.62; H,3.15; N,18.68. Calculated for $C_{10}H_7F_2N_3O$: C,53.8; H,3.16; N,18.82.

(iii) Preparation of 1-[2-(2,4-Difluorophenyl)-2,3-epoxypropyl]-1H-1,2,4-triazole methanesulphonate

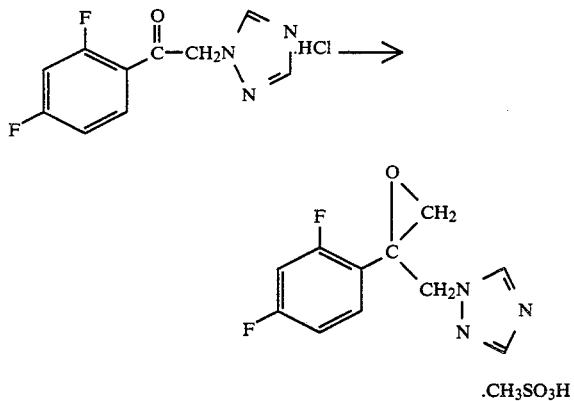

.CH₃SO₃H $2^1,4^1$-Difluoro-2-(1H-1,2,4-triazol-1-yl)acetophenone hydrochloride (59.6 g, 0.23M), trimethylsulphoxonium iodide (50.6 g, 0.23M) and cetrimide (2.1 g) were stirred in a mixture of toluene (370 ml) and 20% w/w aqueous sodium hydroxide at 60° for 3 hours. The toluene layer was separated and concentrated to 110 ml then diluted with ethyl acetate (150 ml). A solution of methanesulphonic acid (16.6 g, 0.172M) in ethyl acetate (20 ml) was added. More ethyl acetate (100 ml) was added and the mixture was stirred at 0° C. for one hour then filtration of the precipitate gave the title compound (43 g, 56%).

20 g of the crude product was dissolved in hot industrial methylated spirits (140 ml) and carbon (2 g) was added. After stirring for 5 minutes, the mixture was filtered and the filtrate was concentrated to 100 ml then the mixture was stirred at 0° C. for one hour. Filtration gave the title compound (7.8 g, 39%), melting point 128°–129° C. The IR (KBr) and nmr (DMSO) were consistent with the desired structure.

Analysis %: Found: C,42.83; H,3.92; N,12.96. Calculated for $C_{12}H_{13}F_2N_3O_4S$: C,43.2; H,3.9; N,12.6.

PREPARATION 7

The following oxirane, m.p. 47°–48°, was prepared similarly to the previous Preparation part (iii) from corresponding starting materials:

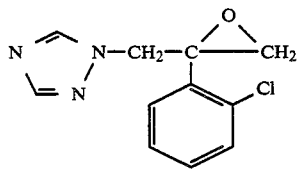

N.m.r. (CDCl₃), δ=8.0,(s),1H; 7.83,(s),1H; 7.2,(m),4H; 4.88(d),J15 Hz,1H; 4.47,(d),J15 Hz,1H; 2.90,(s),2H.

The ketone starting material needed to prepare this oxirane was prepared according to part (ii) of the previous Preparation but using acetone as the solvent at room temperature.

PREPARATION 8

By the methods of above Preparations 3 and 6, the following oxiranes are prepared from the corresponding appropriately substituted 2-(1H-1,2,4-triazol-1-yl)acetophenone:

2-(1H-1,2,4-triazol-1-ylmethyl)-2-(3-trifluoromethylphenyl)oxirane;
2-(1H-1,2,4-triazol-1-ylmethyl)-2-(4-trifluoromethylphenyl)oxirane;
2-(1H-1,2,4-triazol-1-ylmethyl)-2-(4-chlorophenyl)oxirane;
2-(1H-1,2,4-triazol-1-ylmethyl)-2-(4-bromophenyl)oxirane;
2-(1H-1,2,4-triazol-1-ylmethyl)-2-(4-fluorophenyl)oxirane;
2-(1H-1,2,4-triazol-1-ylmethyl)-2-(2,4,6-trifluorophenyl)oxirane; and
2-(1H-1,2,4-triazol-1-ylmethyl)-2-(4-bromo-2,5-difluorophenyl)oxirane.

When there is no ortho-substituent on the phenyl group, the method of Preparation 6 is preferred.

PREPARATION 9

By the method of Preparation 3, the corresponding oxiranes are converted to:

2-(2,4-difluorophenyl)-3-(2-carboxyethylthio)-1-(1H-1,2,4-triazol-1-yl)propan-2-ol;
2-(3-trifluoromethylphenyl)-3-(2-carboxyethylthio)-1-(1H-1,2,4-triazol-1-yl)propan-2-ol;
2-(4-chlorophenyl)-3-(2-carboxyethylthio)-1-(1H-1,2,4-triazol-1-yl)propan-2-ol;
2-(4-bromophenyl)-3-(2-carboxyethylthio)-1-(1H-1,2,4-triazol-1-yl)propan-2-ol;
2-(4-fluorophenyl)-3-(2-carboxyethylthio)-1-(1H-1,2,4-triazol-1-yl)propan-2-ol; and
2-(4-bromo-2,5-difluoro)-3-(2-carboxyethylthio)-1-(1H-1,2,4-triazol-1-yl)propan-2-ol.

Substituting an equivalent quantity of 2-mercaptoacetic acid for 3-mercaptopropionic acid in Preparation 3 produces 2-(2,4-dichlorophenyl)-3-(carboxymethylthio)-1-(1H-1,2,4-triazol-1-yl)propan-2-ol.

We claim:

1. A pharmaceutical composition suitable for oral, parenteral or topical treatment of a susceptible fungal infection in man which comprises a pharmaceutical carrier and an antifungal amount of a compound of the formula

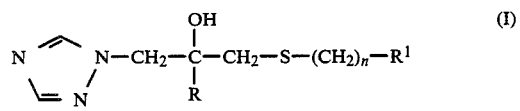

where
R is a phenyl group optionally substituted by 1 to 3 substituents each independently selected from halo, CF₃, C₁-C₄ alkyl and C₁-C₄ alkoxy;
R¹ is selected from (a) —SO.(C₁-C₄ alkyl), (b) —SO₂(C₁-C₄ alkyl), (c) —SO₂NR²R³ where either R² and R³ are both C₁-C₄ alkyl, or R² and R³ together with the N atom to which they are attached represent piperidino, (d) —NHSO₂(C₁-C₄ alkyl) and (e) —CONR⁴R⁵ where either R⁴ is H or C₁-C₄ alkyl and R⁵ is C₁-C₄ alkyl, or R⁴ and R⁵ together with the N atom to which they are attached represent piperidino; and
n is 1 or 2; with the proviso that n is 2 when R¹ is —NHSO₂(C₁-C₄ alkyl);
or a pharmaceutically acceptable or agriculturally acceptable acid addition salt thereof.

2. A composition according to claim 1, wherein R is phenyl substituted by 1 to 3 substituents which are each independently halo or $CF_3$.

3. A composition according to claim 2, wherein R is phenyl substituted by 4-fluoro, 4-chloro, 4-bromo, 2,4-dichloro, 2,4-difluoro, 2,4,6-trifluoro or 4-bromo-2,5-difluoro.

4. A composition according to claim 3 wherein R is 2,4-dichloro.

5. A composition according to claim 4 wherein n is 1 and $R^1$ is $-SO(C_1-C_4$ alkyl), $-SO_2-(C_1-C_4$ alkyl), or $-SO_2NR^4R^5$.

6. The composition of claim 5 wherein $R^1$ is $-SOCH_3$.

7. The composition of claim 5 wherein $R^1$ is $-SO_2CH_3$.

8. The composition of claim 5 wherein $R^1$ is

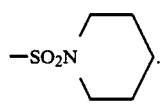

9. A composition according to claim 4 wherein n is 2 and $R^1$ is $-NHSO_2(C_1-C_4$ alkyl).

10. The composition of claim 9 wherein $R^1$ is $-NHSO_2CH_3$.

11. A composition according to claim 4 wherein n is 2 and $R^1$ is $-CONR^4R^5$.

12. The composition of claim 11 wherein $R^1$ is $-CON(CH_3)_2$.

13. The composition of claim 11 wherein $R^1$ is $-CONH(CH_2)_3CH_3$.

14. The composition of claim 11 wherein $R^1$ is $-CON(C_2H_5)_2$.

15. The composition of claim 11 wherein $R^1$ is

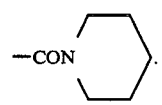

16. A method of treating a susceptible fungal infection in man which comprises oral, parenteral or topical administration to said man of an antifungal amount of a composition of claim 1.

17. An agricultural composition suitable for eradicating or preventing a susceptible fungal infection in a plant or in plant seed which comprises an agriculturally acceptable carrier and an antifungal amount of a compound of the formula

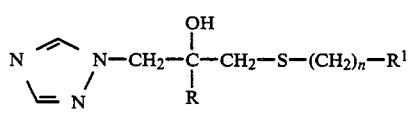

where

R is a phenyl group optionally substituted by 1 to 3 substituents each independently selected from halo, $CF_3$, $C_1-C_4$ alkyl and $C_1-C_4$ alkoxy;

$R^1$ is selected from (a) $-SO(C_1-C_4$ alkyl), (b) $-SO_2(C_1-C_4$ alkyl), (c) $-SO_2NR^2R^3$ where either $R^2$ and $R^3$ are both $C_1-C_4$ alkyl, or $R^2$ and $R^3$ together with the N atom to which they are attached represent piperidino, (d) $-NHSO_2(C_1-C_4$ alkyl) and (e) $-CONHR^4R^5$ where either $R^4$ is H or $C_1-C_4$ alkyl and $R^5$ is $C_1-C_4$ alkyl, or $R^4$ and $R^5$ together with the N atom to which they are attached represent piperidino; and n is 1 or 2; with the proviso that n is 2 when $R^1$ is $-NHSO_2-(C_1-C_4$ alkyl);

or an agriculturally acceptable acid addition salt thereof.

18. A composition according to claim 17, wherein R is phenyl substituted by 1 to 3 substituents which are each independently halo or $CF_3$.

19. A composition according to claim 18, wherein R is phenyl substituted by 4-fluoro, 4-chloro, 4-bromo, 2,4-dichloro, 2,4-difluoro, 2,4,6-trifluoro or 4-bromo-2,5-difluoro.

20. A composition according to claim 19 wherein R is 2,4-dichloro.

21. A composition according to claim 20 wherein n is 1 and $R^1$ is $-SO-(C_1-C_4$ alkyl), $-SO_2-(C_1-C_4$ alkyl), or $-SO_2NR^4R^5$.

22. The composition of claim 21 wherein $R^1$ is $-SOCH_3$.

23. The composition of claim 21 wherein $R^1$ is $-SO_2CH_3$.

24. The composition of claim 21 wherein $R^1$ is

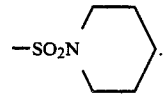

25. A composition according to claim 20, wherein n is 2 and $R^1$ is $-NHSO_2(C_1-C_4$ alkyl).

26. The composition of claim 25 wherein $R^1$ is $-NHSO_2CH_3$.

27. A composition according to claim 20 wherein n is 2 and $R^1$ is $-CONR^4R^5$.

28. The composition of claim 27 wherein $R^1$ is $-CON(CH_3)_2$.

29. The composition of claim 27, wherein $R^1$ is $-CONH(CH_2)_3CH_3$.

30. The composition of claim 27 wherein $R^1$ is $-CON(C_2H_5)_2$.

31. The composition of claim 27 wherein $R^1$ is

32. A method of eradicating or preventing a susceptible fungal infection in a plant or in plant seeds which comprises treating said plant or said seeds with an antifungal amount of a composition of claim 17.

* * * * *